(12) United States Patent
Shumate et al.

(10) Patent No.: US 9,186,064 B2
(45) Date of Patent: Nov. 17, 2015

(54) INTERNAL OPTICAL SPECTROSCOPE AND METHOD FOR REAL TIME IN-SITU DIAGNOSIS IN LIVING CELLS

(71) Applicant: The United States of America as Represented by the Secretary of the Army, Washington, DC (US)

(72) Inventors: Daniel Lee Shumate, Huntsville, AL (US); Paul B Ruffin, Harvest, AL (US); Wayne Davenport, Owens Cross Roads, AL (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 326 days.

(21) Appl. No.: 13/970,665

(22) Filed: Aug. 20, 2013

(65) Prior Publication Data
US 2015/0057553 A1    Feb. 26, 2015

(51) Int. Cl.
*A61B 6/00*    (2006.01)
*A61B 5/00*    (2006.01)
*A61B 10/02*    (2006.01)

(52) U.S. Cl.
CPC ............. *A61B 5/0071* (2013.01); *A61B 5/0084* (2013.01); *A61B 5/6848* (2013.01); *A61B 10/0233* (2013.01)

(58) Field of Classification Search
CPC .................................................... A61B 5/0066
USPC ......................................................... 600/478
See application file for complete search history.

(56) References Cited

U.S. PATENT DOCUMENTS

| | | | |
|---|---|---|---|
| 5,858,781 A | 1/1999 | Matyas | |
| 5,866,417 A | 2/1999 | Matyas | |
| 6,445,939 B1* | 9/2002 | Swanson | A61B 5/0066 385/33 |
| 6,564,087 B1* | 5/2003 | Pitris | A61B 1/00183 600/478 |
| 2005/0203419 A1 | 9/2005 | Ramanujam | |
| 2008/0243031 A1* | 10/2008 | Seibel | A61B 1/0008 600/566 |
| 2009/0323076 A1* | 12/2009 | Li | A61B 5/0066 356/479 |
| 2011/0098531 A1* | 4/2011 | To | A61B 1/32 600/114 |
| 2012/0123244 A1* | 5/2012 | Hashimshony | A61B 5/4312 600/415 |

FOREIGN PATENT DOCUMENTS

CA       2479349       9/2003

OTHER PUBLICATIONS

Brian M. Cullum, Guy D. Griffin, and Tuan Vo-Dinh; Nanosensors: Design and Application to Site-Specific Cellular Analyses; SPIE Proceedings, May 2002, vol. 4615, pp. 148-154.
Tuan Vo-Dinh and Paul Kasili; Fiber-Optic Nanosensors for Single-Cell Monitoring; Analytical and Bioanalytical Chemistry Journal, Springer-Verlag 2005.

* cited by examiner

*Primary Examiner* — Joel F Brutus
(74) *Attorney, Agent, or Firm* — W. B. Haymond

(57) ABSTRACT

The present application relates to an internal optical spectroscope comprising: a needle sleeve insertable into and removable from targeted living tissue; a shaft housed by the needle sleeve including at least one v-shaped trough including an aft side and a next-to-aft side; a light source comprising variable light wave lengths of both visible and near infrared light; at least one light transmission fiber comprising a transmitting end; at least one light detector fiber comprising a receptive end; and data processor. The present application also relates to a method of performing an optical biopsy in situ.

18 Claims, 7 Drawing Sheets

INTERNAL OPTICAL SPECTROSCOPE AND METHOD FOR REAL TIME IN-SITU DIAGNOSIS IN LIVING CELLS

BACKGROUND

The conventional practice in suspected cancer diagnosis is to take a biopsy of the area in question for microscopic study at another place and time. Besides being invasive and traumatic, this technique requires several steps which can be time consuming and subject to error.

BRIEF DESCRIPTION OF THE DRAWINGS

Features and advantages of embodiments of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
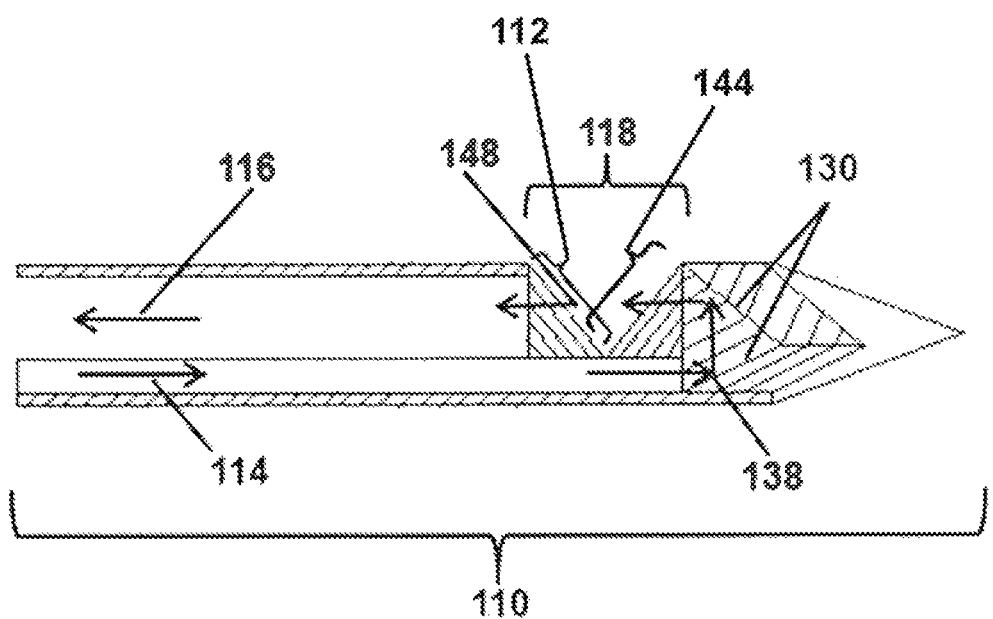
FIG. 1 is a lateral section view of an embodiment of the present application showing the shaft of the internal optical spectroscope.

The present application discloses a means to assess living tissue samples with excellent measurement accuracy by assessing a dimensional sample in situ. This application will allow doctors to observe and study living tissue (at the cellular level) in real time, while minimizing the trauma to the areas surrounding the site of the living tissues studied. In many cases, this will help eliminate the need of invasive and repeated biopsies, while improving the quality of the available data and the repeatability of the test. Additionally, this application can be used in the study of the bonding and growth of critical cellular areas (e.g. nerve cell growth, attaching areas, and micro cellular surgery), by allowing a real time inspection of such critical areas.

A molecule is said to fluoresce when it absorbs light energy (photons) from the UV-visible spectrum, via a process known as excitation, and then rapidly emits (reradiates) light energy at a longer wavelength than the original light absorbed, as the molecule returns back to its ground state. The difference between the excitation and re-radiated emission intensity wavelengths is known as the Stokes shift. The primary advantage of fluorescence over absorption and radioactivity spectroscopy is the ability of fluorescence to separate molecules on the basis of either or both their excitation or emission spectra rather than using just a single spectrum as is used in absorption and radioactivity spectroscopy. It has been shown, for example, that human cancer cells fluoresce much more (i.e., emit much more red light) than noncancerous cells.

In the present application, at least one thin fold of tissue to be examined is squeezed into a narrow trough of precise dimensions in between the two trough sides. This offers an enormous improvement in measurement accuracy.

The present application provides a means for medical professionals to assess internal tissue layers without the necessity of removing tissue (which causes a wound that requires healing). The present application makes it possible to observe living tissue fluorescence at specific wavelengths.

The present application relates to an internal optical spectroscope comprising several elements (not in any particular order).

The first element is a needle sleeve comprising a shaft, the needle sleeve being insertable into and removable from targeted living tissue.

The second element of the internal optical spectroscope is the shaft housed by the needle sleeve. The shaft comprises a cylinder with a pointed insertion end and at least one v-shaped notch (trough) in the cylinder. The v-shaped trough includes an aft side and a next-to-aft side. The shaft is capable of being at least partially pushed out of the needle sleeve and into the targeted living tissue after the needle sleeve has already been inserted into the targeted living tissue. The shaft is also capable of being pulled out of the living tissue and back into the needle sleeve when the needle sleeve is still in the targeted living tissue. The at least one v-shaped trough in the shaft is capable of holding at least one fold of living tissue in the shaft, while the shaft is in the targeted internal living tissue, without substantially damaging the living tissue.

The third element of the internal optical spectroscope is a light source comprising variable light wave lengths of both visible and near infrared light.

The fourth element of the internal optical spectroscope is at least one light transmission fiber comprising a transmitting end (illuminator), through which light streams out, of the transmitting fiber or fibers. The at least one light transmission fiber is connected to the light source and stretches along a length of the shaft. The light source is capable of sending light through the at least one light transmission fiber with the transmitting end (illuminator) of the fiber or fibers positioned on either the next-to-aft side or the aft side of the v-shaped trough. The light escapes directly out of the transmitting end (illuminator) and into the v-shaped trough, the light traveling across the v-shaped trough. The light from the transmitting end (illuminator) is capable of penetrating through one side of the tissue in the trough and causing the tissue to fluoresce light out of the opposite side of the tissue while the tissue is held in the v-shaped trough.

The fifth element of the internal optical spectroscope is at least one light detector fiber comprising a receptive end (receptor) of the detector fiber or fibers. The receptive end receives light from the trough and is positioned on the opposite side of the v-shaped notch from the transmitting end (illuminator). The at least one light detector fiber stretches from the receptive end along the screw shaft to a data processor. The receptive end is capable of receiving the reflected light from the fluoresced tissue and transmitting an optical signal to the data processor.

The sixth element of the internal optical spectroscope is the data processor.

In one embodiment of the above application, a "screw" design concept was used which permitted good measurement accuracy by assessing a dimensional sample. In this embodiment, the internal optical spectroscopic unit, which enables the performance of optical biopsies, included an actuated, spirally threaded shaft, which moves back and forth inside an 18-25 gauge needle sleeve (sheath) via clockwise and counter-clockwise rotations. The operation of the spectroscopic unit is similar to a syringe drive, which consists of a piston pump with a plunger (a threaded shaft in this case) that is able to be pulled and pushed along inside a cylindrical tube/barrel (the 18-25 gauge needle sleeve in this case) and to be able to be at least partially pushed out of the cylindrical tube/barrel. The shaft threads can be tailored/designed to form trough(s) between threads which fit a suspect tissue sample of precise dimensions (depth/thickness, width, and length), and which permit improved measurement accuracy. The response of living tissue to various wavelengths of light is examined by transmitting optical light energy to the specified area through thin optical fibers. These optical fibers were firmly attached to the shaft of the threaded screw and terminated to form an illuminator at the next-to-aft screw thread. The next-to-aft screw thread is directly adjacent to the aft thread (the last thread that light can encounter on the shaft). The next-to-aft and aft threads form a trough. The incident source light in the illuminator exits the fibers, enters the trough and is transmitted through at least one fold of tissue sandwiched/squeezed between the aft and next-to-aft threads of the threaded shaft, the two threads forming the trough. The molecules in the tissue cells become excited from the incident light and re-emit the light at a longer wavelength or fluorescence. The fluoresced light encounters a mirror-like reflector surface on the opposite (aft) screw thread of the trough formed by the aft thread and the next-to-aft thread. The reflected light is collected at a receptor on the aft thread near to the mirror-like reflector surface. The receptor is connected to and forms the end of the detector fibers. The detector fibers transmit the signal from the receptor to a data processor. Signal detection is accomplished via the suspect tissue cells' spectroscopic signature, which can denote malignancy or benignity.

In this embodiment, a needle sleeve-encased shaft (0.5 to 1.0 mm) with screw threads is used. The shaft with screw threads can be embedded into tissue. As the shaft is screwed into the tissue, the tissue is squeezed between the aft and next-to-aft threads of the threaded shaft to permit spectroscopic measurements at the micron level without substantially damaging the living tissue.

The at least one optical fiber is selected to optimize light transmission in both the visible portion of the spectrum and the near infrared portion of the spectrum. Therefore, visible light penetrates a few mm through the at least one tissue fold, whereas near infrared (IR) light penetrates a few cm through the at least one tissue fold. The thickness of the at least one tissue fold in the trough in the present application is much less than 1 mm.

FIG. 1 shows a lateral section view of a schematic of one embodiment of the present application. Light is transmitted through optical fiber(s) 114 on the threadless shaft 110, exits the at least one optical fiber 114 at the illuminator end 138, and encounters a right angle mirror 130 near the illuminator end 138, which permits two right angle reflections of the light, resulting in the reflected light being transmitted through the aft side 144 and into a v-shaped notch (trough) 118. The size of the v-shaped notch (trough) 118 determines the depth and width of any tissue fold 156 that may be held in the v-shaped notch 118. The data is captured by a receptor 148, located opposite the aft side 144 on the next-to-aft side 112 of the v-shaped notch 118. The receptor 148 in turn is connected to at least one detector fiber 116.

Figure 2:
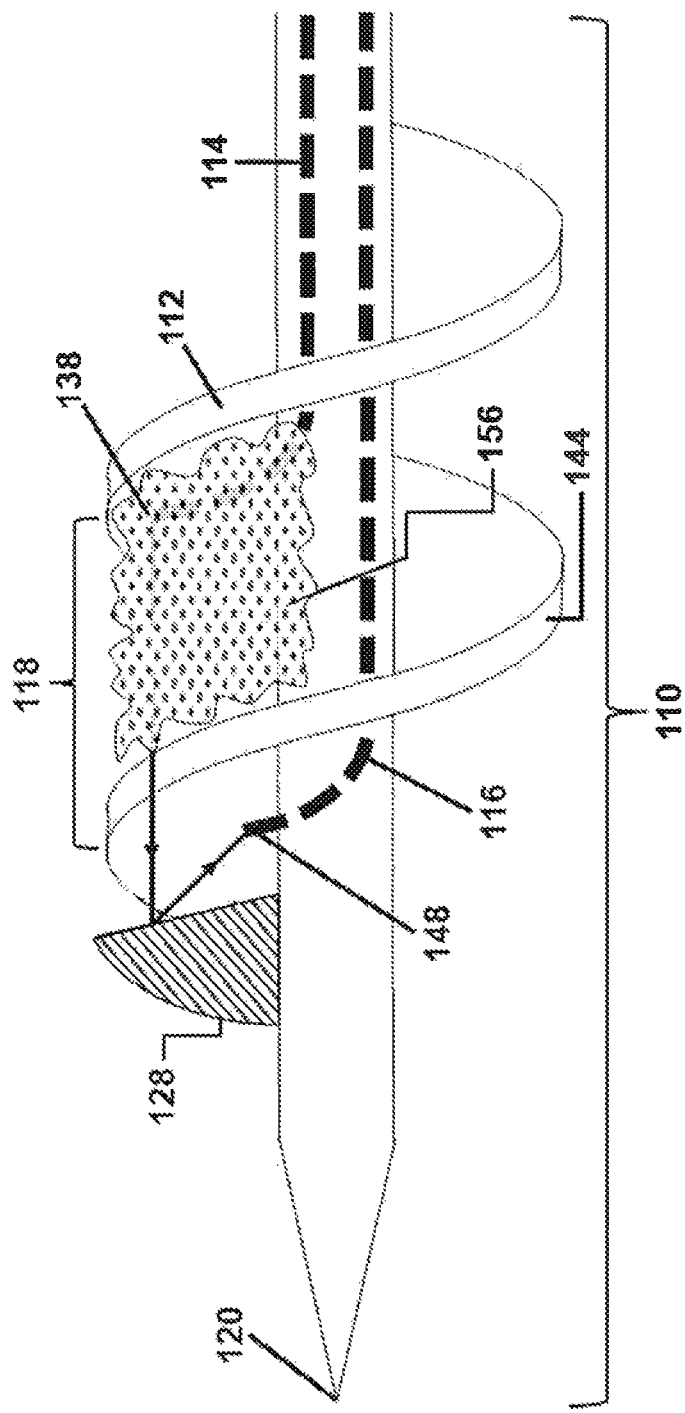
FIG. 2 is a schematic of an embodiment of the present application showing the threaded shaft with the two threads which form the trough of the internal optical spectroscope.

FIG. 2 is a close-up schematic view of the front end of the threaded shaft 110, according to a "screw design" embodiment of the application, showing the at least one source fiber 114 extending along the shaft 110 to the next-to-aft thread 112 ending in an illuminator 138. The rim of the next-to-aft thread 112 is outlined but the inner part of the thread 112 is cut away in the drawing to permit a better view of the inside of the trough 118. The diagram also shows the aft thread 144 and the next-to-aft thread 112 situated on the shaft 110 near to the pointed insertion end 120, a tissue portion 156 situated in the trough 118 formed between the next-to-aft thread 112 and the aft thread 144. Like the next-to-aft thread 112, the rim of the aft thread 144 is outlined but the inner part of the thread 144 is cut away to permit a better view of the inside of the trough 118. The reflector 128 is also shown situated in a position on the aft thread 144. The receptor end 148 of the at least one detector fiber 116 is shown in a position close to the reflector 128 on the aft thread 144. The at least one detector fiber 116 is shown continuing on along the threaded shaft 110.

Figure 3:
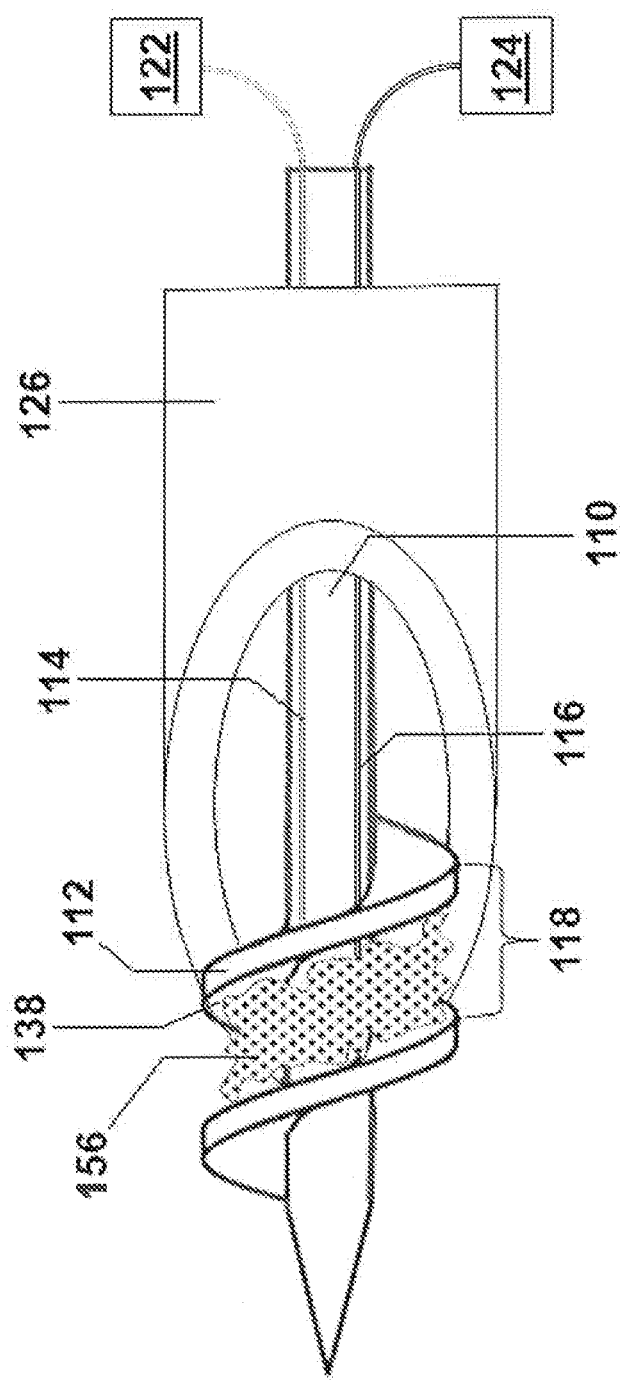
FIG. 3 shows an embodiment of the present application with a view toward the illuminator on the next-to-aft thread in the trough.

FIG. 3 shows an aspect of the "screw design" embodiment of the present application. A portion of the optical spectroscopy system for real-time tissue diagnosis is shown from a perspective that faces the illuminator 138 on the next-to aft side 112 of the trough 118. Specifically shown are an optical power source 122, optical transmission fibers 114, the illuminator 138, and the detector (receiving) fibers 116 that are hard-mounted to the screw shaft 110, and a data processor 124 for data collection. FIG. 3 also shows the micro-needle sleeve 126 housing the screw shaft 110.

Figure 4:
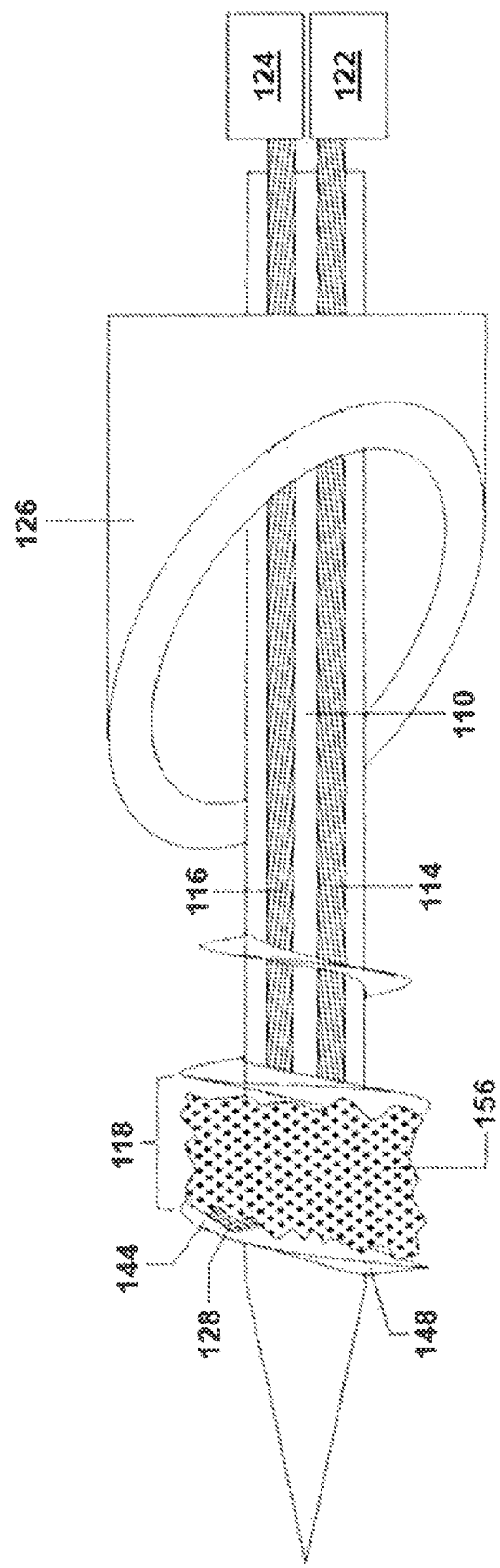
FIG. 4 is an embodiment of the present application with a view toward the reflector and receptor on the aft thread in the trough.

FIG. 4 shows a similar aspect of the "screw design" embodiment as in FIG. 3 but from a perspective that faces the reflector 128 on the aft side 144 of the trough 118. It shows the screw shaft 110 being housed inside an 18-25 gauge needle sleeve 126. It consists of an optical power source 122, optical transmission fibers 114, the reflector 128, the receptor 148, a tissue portion 156, detector (receiving) fibers 116 that are hard-mounted to the screw shaft 110 and a data processor 124.

Figure 5:
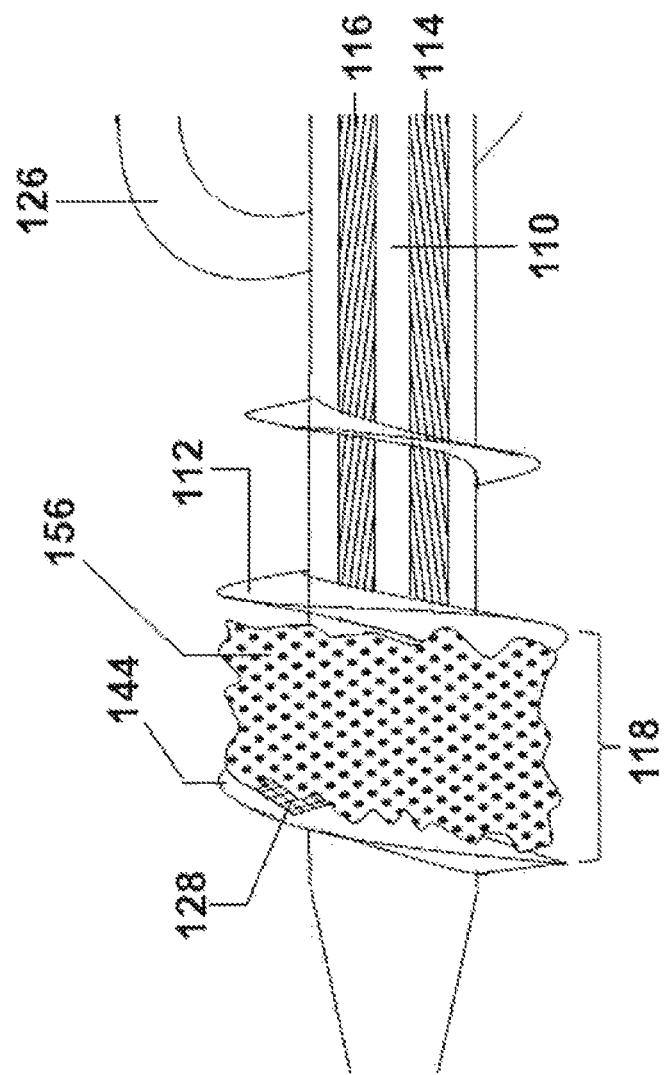
FIG. 5 is a close-up view of an embodiment of the present application, showing the illuminator, reflector and receptor in the trough.

FIG. 5 shows a view of a similar aspect of the "screw design" embodiment as in FIG. 4 but more close range. It shows the screw shaft 110 with a thin strip of tissue 156 held between the aft thread 144 and the next-to-aft thread 112 of trough 118 formed in the shaft 110. The micro-needle sleeve 126 is inserted into the suspect tissue area for real-time inspection of the targeted living tissue. Once the tip of the micro-needle sleeve 126 is positioned inside the suspect tissue area, the retracted screw shaft 110 can be pushed out of the needle sleeve 126 as shown in FIG. 5, by rotation of the screw shaft 110. The rotating screw motion causes at least one thin fold of tissue 156 to be squeezed into the trough 118 between the next-to-aft screw thread 112 and the aft screw thread 144. Light is transmitted through the at least one optical transmission fiber 114. The at least one optical transmission fiber 114 terminates at the illuminator 138 on the next-to-aft screw thread 112 on the surface of the trough 118. The illuminator 138 at the end of the optical transmission fiber 114 sends light into the trough 118 causing the tissue fold 156 to fluoresce. The at least one tissue fold 156 that is sandwiched between the next-to-last screw thread 112 and the last screw thread 144 is fully illuminated by the light produced from multiple light transmission fibers 114. The interaction of the light with the molecules in the suspect tissue cells causes the at least one tissue fold 156 to fluoresce. The fluoresced light encounters the reflector area 128 on the opposite (aft) screw thread 144. The reflected light from the reflector area 128 is captured by the receptor end 148 of the detector fibers 116 near the reflector area 128. The receptor 148 transmits the optical signal through the detector fibers 116. Thus, spectroscopic imaging is accomplished via computing the fluorescence response of the at least one tissue fold specimen 156 to a spectrum of optical energy. A library of data can be created by testing known tissue cells to be used in the determination of malignancy or benignity. The result will provide the doctor/examiner with real time diagnosis.

Figure 6:
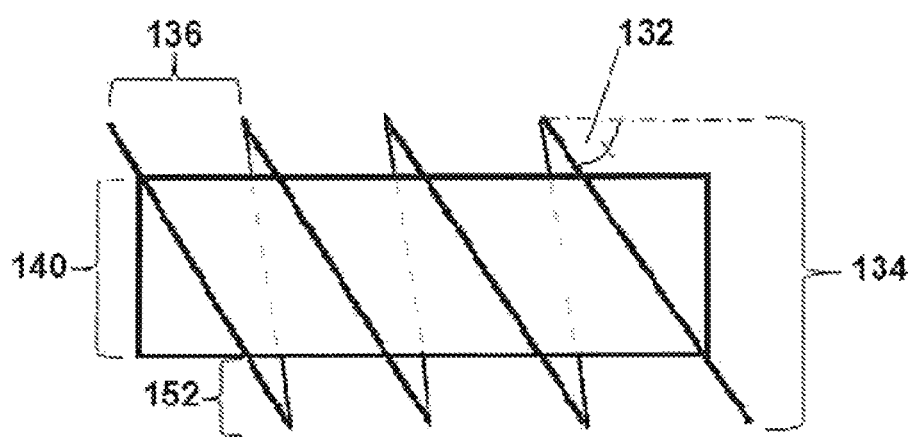
FIG. 6 is a lateral view of a threaded screw analogous to the threads of the shaft in an embodiment of the present application.

FIG. 6 shows the design parameters (pitch 136, flight depth 152, major diameter 134, minor diameter 140, and helix angle 132) for a threaded screw which is analogous to the threaded shaft 110 of the present application. The dimensions (L×W×t) of the at least one tissue fold sample 156 can be accurately measured. The Helical Length (L) is:

$$L=\sqrt{[(2\pi r)^2+p^2]},$$

where r=D/2 is screw radius, D is the major diameter 134 of external thread, and p is the pitch 136; the Width (W) is $$W=r-r_0,$$

where $r_0$=d/2; d is the minor diameter of the internal thread 140; and the Thickness (t) is $$t=p.$$

Figure 7:
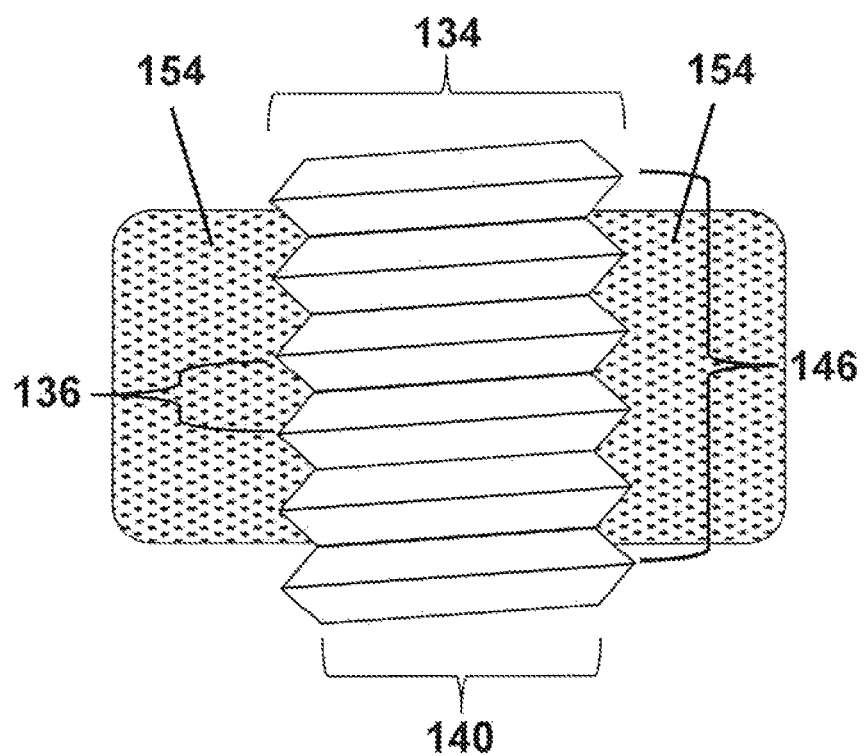
FIG. 7 is a lateral section view of a threaded screw surrounded by a female nut, analogous to the threaded shaft with living tissue squeezed into the shaft troughs in an embodiment of the present application.

FIG. 7 shows a lateral section view of a screw with screw threads 146 screwed into a nut having female nut threads 154. The screw threads 146 with female nut threads 154 in FIG. 7 are approximately analogous to the threaded shaft 110 positioned in the midst of the living tissue where the shaft 110 has been screwed/inserted.

The present application relates to an internal optical spectroscope comprising several elements (not in any particular order).

The first element is a needle sleeve 126 comprising a shaft 110, the needle sleeve 126 being insertable into and removable from targeted living tissue.

The second element of the internal optical spectroscope is the shaft 110 housed by the needle sleeve 126. The shaft 110 comprises a pointed insertion end 120 and at least one v-shaped trough including an aft side 144 and a next-to-aft side 112. The shaft 110 is capable of being pushed out of the needle sleeve 126 and into the targeted living tissue after the needle sleeve 126 has already been inserted into the targeted living tissue. The shaft 110 is also capable of being pulled out of the living tissue and back into the needle sleeve 126 when the needle sleeve 126 is in the targeted living tissue. The at least one v-shaped trough 118 in the shaft 126 is capable of holding at least one fold 156 of living tissue while the shaft 110 is in the targeted living tissue.

The third element of the internal optical spectroscope is a light source 122 comprising variable light wave lengths of both visible and near infrared light.

The fourth element of the internal optical spectroscope is at least one light transmission fiber 114 comprising a transmitting end (illuminator) 138. The at least one light transmission fiber 114 is connected to the light source 122 and stretches along a length of the shaft 110. The light source 110 is capable of sending light through the at least one light transmission fiber 114 with the transmitting end (illuminator) 138 attached to the next-to-aft side 112 or the aft side 144 of the v-shaped trough 118. The light escapes directly out of the transmitting end (illuminator) 138 and into the v-shaped trough 118 from the next-to-aft side or the aft side of the v-shaped trough, the light traveling from the transmitting end 138 across the v-shaped trough 118. The light is capable of penetrating through the at least one fold 156 of tissue held in the v-shaped trough 118 and causing the at least one fold 156 of tissue to fluoresce light as the at least one fold 156 of tissue is held in the v-shaped trough 118.

The fifth element of the internal optical spectroscope is at least one light detector fiber 114 comprising a receptive end (receptor) 148. The receptive end (receptor) 148 is positioned on an opposite side of the v-shaped trough 118 from the transmitting end (illuminator) 138. The at least one light detector fiber 116 stretches from the receptive end 148 along the shaft 110 to a data processor 124. The receptive end 148 is capable of receiving the reflected light from the at least one fold 156 of fluoresced tissue and transmitting an optical signal to the data processor 124.

The sixth element of the internal optical spectroscope is the data processor 124.

In another embodiment of the internal optical spectroscope of the present application, the transmitting end 138 of the at least one light transmission fiber 114 is attached at the next-to-aft side 112 of the v-shaped trough 118, so that the light escapes directly out of the transmitting end 138 on the next-to-aft side 112 into the v-shaped trough 118.

In a related embodiment of the internal optical spectroscope of the present application, on the aft side 144 of the v-shaped trough 118 opposite the transmitting end 138, there are a mirror-like reflector surface 128 and the receptive end 148 of the at least one detector fiber 116.

In still another embodiment of the internal optical spectroscope of the present application, the shaft 110 comprises screw threads 146 extending spirally along the outside surface of the shaft 110, with the at least one v-shaped trough 118 formed between aft 144 and next-to-aft 112 threads. The screw shaft 110 is capable of being pushed out of the needle sleeve 126 and screwed into the targeted living tissue when the needle sleeve 126 is in the targeted living tissue. The screw shaft 110 also is capable of being unscrewed out of the living tissue and back into the needle sleeve 126 when the needle sleeve 126 is in the targeted living tissue.

In another embodiment of the internal optical spectroscope of the present application, the transmitting end 138 of the at least one light transmission fiber 114 is positioned near to the aft side 144 so that the light escapes out of the transmitting end 138 to a right angle mirror 130 which directs the light to escape out of the aft side 144 of the v-shaped trough 118.

In yet another embodiment of the internal optical spectroscope of the present application, the receptive end 148 of the at least one light detector fiber 114 is on the next-to-aft side 112 of the v-shaped trough 118.

In yet another embodiment of the internal optical spectroscope, the at least one fold 156 of tissue in the transmitting trough 118 of the internal optical spectroscope is less than 1.0 mm thick.

In still another embodiment of the internal optical spectroscope, the distance from rim to rim between the next-to-last thread 112 and the last thread 144 of the internal optical spectroscope is less than 3.08 mm.

In another embodiment of the internal optical spectroscope, the distance between the reflector surface 128 and the receptive end 148 of the at least one receptor fiber 116 is no more than 1.0 mm.

The present application also relates to a method of performing an optical biopsy in situ on targeted living tissue.

The first step of the method of performing an optical biopsy is inserting a needle sleeve 126 of an internal optical spectroscope into targeted living tissue. The needle sleeve 126 holds a shaft 110. The shaft 110 includes a pointed insertion end 120 and at least one v-shaped trough 118 including an aft side 144 and a next-to-aft side 112.

The second step of the method of performing an optical biopsy is pushing the shaft 110 out of the needle sleeve 126 and into the targeted living tissue without substantially damaging the targeted living tissue. The shaft 110 is pushed out of the needle sleeve 126 and is pushed into the targeted living tissue so that the at least one v-shaped trough 118 of the screw shaft 110 holds at least one fold 156 of the living tissue.

The third step of the method of performing an optical biopsy is sending light from a light source 122 comprising variable light wavelengths of both visible and near infrared light. The light is sent through at least one light transmission fiber 114 stretching along a length of the shaft 110. The at least one transmission fiber 114 comprises a transmitting end (illuminator) 138 attached to or positioned near either the next-to-aft side 112 or the aft side 144 of the at least one v-shaped trough 118. The at least one fold 156 of living tissue is held in the v-shaped trough 118, so that the light penetrates through the at least one fold 156 of tissue, causing the at least one fold 156 of tissue to fluoresce light when the at least one fold 156 of tissue is held in the v-shaped trough 118.

The fourth step of the method of performing an optical biopsy is detecting fluoresced light from the at least one fold 156 of living tissue. The fluoresced light is detected by a receptive end (receptor) 148 of at least one light detector fiber 116 attached to an opposite side of the v-shaped trough from the transmitting end (illuminator) 138. The at least one light detector fiber 116 stretches along a length of the shaft 110 to a data processor 124.

The fifth step of the method of performing an optical biopsy is removing the shaft 110 out of the targeted living tissue and back into the needle sleeve 126 without substantially damaging the targeted living tissue.

The sixth step of the method of performing an optical biopsy is withdrawing the needle sleeve 126 from the targeted living tissue.

In another embodiment of the method of performing an optical biopsy, the transmitting end 138 of the at least one light transmission fiber 114 is attached at the next-to-aft side 112 of the v-shaped trough 118. The light escapes directly out of the transmitting end 138 on the next-to-aft side 112 into the v-shaped trough 118.

In yet another embodiment of the method of performing an optical biopsy, after the light is fluoresced from the at least one fold 156 of tissue, the method further comprises a step of reflecting the fluoresced light from the at least one fold 156 of the living tissue in the v-shaped trough 118 using a mirror-like reflector surface 128 on the aft side 144 of the v-shaped trough 118. The fluoresced light from the at least one fold 156 of the living tissue shines onto and is reflected by the mirror-like reflector surface 128 and is detected by the receptive end 148 of at least one light detector fiber 116 which is near the mirror-like receptor surface 128 on the aft side of the v-shaped trough 118.

In an additional embodiment of the method of performing an optical biopsy, the shaft 110 comprises screw threads 146 extending spirally along the outside surface of the shaft 110 to form threads with the at least one v-shaped trough 118 formed between aft 144 and next-to-aft 112 threads. The screw shaft 110 is capable of being at least partially pushed out of the needle sleeve 126 and screwed into the targeted living tissue when the needle sleeve 126 is already in the targeted living tissue. The shaft 110 is also capable of being unscrewed out of the living tissue and back into the needle sleeve 126 when the needle sleeve 126 is in the targeted living tissue.

In yet another embodiment of the method of performing an optical biopsy, the transmitting end 138 of the at least one light transmission fiber 114 is positioned near to the aft side 144 so that the light escapes out of the transmitting end 138 to a right angle mirror 130 which directs the light to escape out of the aft side 144 of the v-shaped trough 118 toward the next-to-aft side 144.

In still another embodiment of the method of performing an optical biopsy, the receptive end 148 is on the next-to-aft side 112 of the v-shaped trough 118.

In yet another embodiment of the method of performing an optical biopsy, the at least one fold 156 of tissue in the v-shaped trough 118 is less than 1.0 mm thick.

In still another embodiment of the method of performing an optical biopsy, the distance from rim to rim between the next-to-aft side 112 and the aft side 144 is less than 3.08 mm.

In another embodiment of the method of performing an optical biopsy, the distance between the reflector surface 128 and the receptive end 148 is no more than 1.0 mm.

The present application relates to an internal optical spectroscope comprising several elements (not in any particular order).

The first element is a needle sleeve 126 comprising a screw shaft 110, the needle sleeve 126 being insertable into and removable from targeted living tissue;

The second element of the internal optical spectroscope is the screw shaft 110 housed by the needle sleeve 126. The screw shaft 110 is capable of being at least partially pushed out of the needle sleeve 126 and screwed into the targeted living tissue when the needle sleeve 126 is in the targeted living tissue. The screw shaft 110 is also capable of being unscrewed out of the living tissue and back into the needle sleeve 126 when the needle sleeve 126 is in the targeted living tissue. The screw shaft 110 comprises a pointed insertion end 120 and screw threads 146 bonded to the outside surface of the shaft 110. The screw threads 146 extend spirally along the outside surface of the screw shaft 110 to form threads 146, with troughs 118 formed between adjacent screw threads 146. The troughs 118 are capable of holding at least one fold 156 of living tissue in between the adjacent threads 146 while the screw shaft 110 is in the targeted living tissue.

The third element is a light source comprising variable light wave lengths of both visible and near infrared light.

The fourth element is at least one light transmission fiber 114 comprising a transmitting end 138. The at least one light transmission fiber 114 is connected to the light source 122 and stretches along a length of the screw shaft 110. The light source 122 is capable of sending light through the at least one light transmission fiber 114 to the transmitting end 138 positioned at a next-to-aft thread 112 across the trough 118 from the aft thread 144. The aft thread 144 is the last thread the light encounters on the shaft 110. The light escapes out of the transmitting end 138 and into the light transmitting trough 118 between the next-to-aft thread 112 and the aft thread 144. The light is capable of penetrating through the at least one fold 156 of tissue and causing the at least one fold 156 of tissue to fluoresce light when the at least one fold 156 of tissue is held in the light transmitting trough 118.

The fifth element is a mirror-like reflector surface 128 on the aft thread 144 in the light-transmitting trough 118. The mirror-like reflector surface 128 faces the next-to-aft thread 112 across the light transmitting trough 118. The mirror-like reflector surface 128 is capable of reflecting the light from the at least one fold 156 of fluoresced tissue in the light transmitting trough 118.

The sixth element is at least one light detector fiber 116 comprising a receptive end 148. The receptive end 148 is positioned on the aft thread 144 near the mirror-like reflector surface 128 on the aft thread 144. The at least one light detector fiber 116 stretches from the receptive end 148 along the screw shaft 110 to a data processor 124. The receptive end 148 is capable of receiving the reflected light from the mirror-like reflector surface 128 and transmitting an optical signal to the data processor 124.

The seventh element is a data processor.

In still another embodiment of the present application, the distance from rim to rim between the next-to-last thread 112 and the aft thread 144 is less than 3.08 mm.

To verify these methods and configurations, the following experiments were conducted and described in the Examples below.

EXAMPLE

Example 1

An experiment was performed to test the transmission capabilities of at least one detector fiber 116 and to test what materials are viable as the reflector surface 128 on the rim of the aft screw thread 144.

In a horizontal setup, at least one detector fiber 116 and at least one source fiber 114 ran the length of a stabilizer 110. Once they reached the end of the stabilizer 110, they entered a needle sheath 126. At the end of the sheath 126 the at least one detector fiber 116 and the at least one source fiber 114 had a distance of ~1 mm between them and ran essentially parallel to each other. At this junction, the at least one detector fiber 116 and the at least one source fiber 114 were coupled using matching gel. Different reflector surfaces 128 were suspended perpendicularly to the at least one detector 116 and the at least one source 114 fibers.

Two candidate reflector surfaces 128 (out of a total of eight original candidates tested) were chosen for this experiment. A mirror surface and a white surface were found to offer viable reflector surface 128. However, the mirror was superior to the white surface in that it allowed the detector fiber 116 to collect a broader, more powerful spectrum. To prove this, three subtests were completed. With each subtest, a layer of lens cleaning paper was placed between the junction of the at least one source transmission fiber 114 and the at least one receptor fiber 116 and the mirror. The reflector surface 128 became increasingly whiter and decreasingly less mirror-like with each test. A decrease in power accompanied each additional layer. This experiment verified the concept that the signal can be successfully transmitted optically without the use of electrical wire or sensors.

Example 2

An experiment was performed using a vertical setup, as opposed to the horizontal setup discussed in Example 1. The vertical setup differed from the horizontal setup only in orientation. The change in orientation allows for mobility along the stabilizer 110 and for substances to be placed between the junction of the at least one source transmission fiber 114 and the at least one receptor fiber 116 and reflector 128. The purpose of the experiment was to determine what distance between the reflector surface 128 and the at least one detector fiber 116 is optimal for altered spectrum collection. Different distances were achieved by moving the fiber junction relative to the reflector 128 via the mobile part of the stabilizer 110. The optimum distance was found to be ~1.0 mm. The data from this experiment are shown in Table 1.

TABLE 1

| | Vertical Setup Experiment #1 Data | | | |
|---|---|---|---|---|
| Test Number | Distance from Mirror (mm) | Center Power Level (dB) | Amount of Narrowing Relative to Uninterrupted Plot on Shorter $\lambda$ Side (pm) | Amount of Narrowing Relative to Uninterrupted Plot on Longer $\lambda$ Side (pm) |
| Uninterrupted Source (for comparison) | N/A | −38.0 | N/A | N/A |
| 1 | 0.0 | −67.0 | ~7.494 | ~7.494 |
| 2 | 0.5 | −63.0 | ~4.996 | ~4.996 |
| 3 | 1.0 | −59.0 | ~0.000 | ~4.996 |
| 4 | 1.5 | −73.0 | ~9.992 | ~9.992 |
| 5 | 2.0 | −74.0 | ~9.992 | ~9.992 |

Example 3

An experiment was performed using the vertical setup to test the transmission abilities of the at least one light source fiber 114 when a substance was placed between the junction of the transmission fiber 114 and the transmission fiber 116 and the reflector surface 128 (in this case, a mirror). Tests were performed on common substances such as water, apple juice, orange juice, cake crumbs, bread crumbs, steel, foam soap, Kevlar®, and two types of Styrofoam®. The experiment showed that light from the light fibers 114 was transmissible to the reflector surface 128 through the various substances.

Example 4

An experiment was performed to determine at what distance (bandwidth) between the at least one light source fiber 114 and the at least one detector fiber 116 the transmission abilities of the light beam began to suffer. Power was not as crucial as a broad bandwidth. In this setup, the at least one detector fiber 116 and the at least one source fiber 114 were placed directly across from each other and were aligned using a v-groove clamp. Six tests were completed in this experiment. The optimum distance between the at least one detector fiber 116 and the at least one source fiber 114 was found to be ~3.077 mm. Experimental data from this setup is shown in Table 2.

TABLE 2

Direct Setup Data

| Test Number | Distance Between Detector Fiber(s) 116 and Source Fiber(s) 114 (mm) | Center Power Level (dB) | Comments on Change in Plot |
|---|---|---|---|
| 1 | 0.254 | −23.0 | Baseline for Direct Setup |
| 2 | 1.077 | −36.0 | Baseline for Direct Setup |
| 3 | 2.077 | −36.5 | Only decrease in power |
| 4 | 3.077 | −39.0 | Only decrease in power |
| 5 | 4.077 | −39.5 | Narrowing by ~19.987 pm from left side of plot |
| 6 | 5.077 | −61.0 | Narrowing by ~9.992 pm from left side of plot |

Example 5

An experiment was performed to test at what distance the bandwidth of the incoming signal from the at least one light source fiber 114 to the at least one detector fiber 116 began to suffer due to dilution. The findings in this experiment were more precise because the alignment of the large scale model used in this experiment was superior to that of the v-groove clamp used in Example 4. With proper alignment, it was found that the distance between the rims of the aft thread 144 and the next-to-aft thread 112 should be ≤9.5 mm (which corresponds to a distance of ≤5.4.7 mm between the fibers), as opposed to ~3.077 mm. Experimental data from this experiment are shown in Table 3.

TABLE 3

Thread Setup Experiment Data

| Test Number(s) | Distance Between Rim Tips Range (mm) | Distance Mean (mm) | Center Power Level Range (dB) | CPL Range Mean (dB) | Amount of Narrowing Relative to Plot Window on Shorter λ Side (pm) | Amount of Narrowing Relative to Plot Window on Longer λ Side (pm) |
|---|---|---|---|---|---|---|
| 1 | 4.9 | 4.9 | −39.0 | −39.0 | ~19.984 | ~9.992 |
| 2-8 | 5.9-9.5 | 7.4 | −58.0-(50.0) | −54.3 | ~19.984 | ~9.992 |
| 9-10 | 10.7-12.9 | 11.8 | −62.0-(−58.0) | −60.0 | ~24.980 | ~14.998 |
| 11-14 | 14.5-20.2 | 17.5 | −68.0-(−62.0) | −65.5 | ~29.976 | ~19.984 |
| 15 | 22.5 | 22.5 | −70.0 | −70.0 | ~29.976 | ~24.980 |
| 16 | 24.4 | 24.4 | −75.0 | −75.0 | ~34.972 | ~29.976 |

While several embodiments have been described in detail, it will be apparent to those skilled in the art that the disclosed embodiments may be modified. Therefore, the foregoing description is to be considered exemplary rather than limiting.

What is claimed is:

1. An internal optical spectroscope comprising:
   a) a needle sleeve comprising a shaft, the needle sleeve being insertable into and removable from targeted living tissue;
   b) the shaft housed by the needle sleeve, the shaft comprising a pointed insertion end and at least one v-shaped trough including an aft side and a next-to-aft side, the shaft is capable of being at least partially pushed out of the needle sleeve and into the targeted living tissue when the needle sleeve is already in the targeted living tissue, and the shaft also is capable of being pulled out of the targeted living tissue and back into the needle sleeve when the needle sleeve is in the targeted living tissue, the at least one v-shaped trough in the shaft being capable of holding at least one fold of the targeted living tissue but not removing or substantially damaging any of the targeted living tissue while the shaft is being pushed out of the needle sleeve into the targeted living tissue, while the shaft is in the targeted living tissue, or while the shaft is be removed from the targeted living tissue; wherein the shaft comprises screw threads extending spirally along the outside surface of the shaft, with the v-shaped trough formed between aft and next-to-aft threads, a screw shaft is capable of being at least partially pushed out of the needle sleeve and screwed into the targeted living tissue when the needle sleeve is in the targeted living tissue, and the screw shaft also is capable of being unscrewed out of the targeted living tissue and back into the needle sleeve when the needle sleeve is in the targeted living tissue
   c) a light source comprising variable light wave lengths of both visible and near infrared light;
   d) at least one light transmission fiber comprising a transmitting end, the at least one light transmission fiber being connected to the light source and stretching along a length of the shaft, the light source being capable of sending light through the at least one light transmission fiber with the transmitting end attached to the next-to-aft side or the aft side of the v-shaped trough, so that the light escapes directly out of the transmitting end into the v-shaped trough from the next-to-aft side or the aft side of the v-shaped trough, the light traveling from the transmitting end across the v-shaped trough, the light being capable of penetrating through the at least one fold of tissue held in the v-shaped trough and causing the at least one fold of tissue to fluoresce light when the at least one fold of tissue is held in the v-shaped trough;
   e) at least one light detector fiber comprising a receptive end, the receptive end being positioned on an opposite side of the v-shaped trough from the side of the transmitting end, the at least one light detector fiber stretching from the receptive end along the shaft to a data processor, the receptive end being capable of receiving fluoresced light from the at least one fold of fluoresced tissue and transmitting an optical signal to the data processor; and
   f) the data processor.

2. The internal optical spectroscope of claim 1, wherein the transmitting end of the at least one light transmission fiber is attached at the next-to-aft side of the v-shaped trough, so that the light escapes directly out of the transmitting end on the next-to-aft side into the v-shaped trough.

3. The internal optical spectroscope of claim 2, wherein, on the aft side of the v-shaped trough opposite the transmitting end, there are a mirror-like reflector surface and the receptive end of the at least one detector fiber.

4. The internal optical spectroscope of claim 3, wherein the distance between the mirror-like reflector surface and the receptive end is no more than 1.0 mm.

5. The internal optical spectroscope of claim 1 wherein the transmitting end of the at least one light transmission fiber is positioned near to the aft side so that the light escapes out of the transmitting end to a right angle mirror which directs the light to escape out of the aft side of the v-shaped trough.

6. The internal optical spectroscope of claim 5, wherein the receptive end of the at least one light detector fiber is on the next-to-aft side of the v-shaped trough.

7. The internal optical spectroscope of claim 1, wherein the at least one fold of tissue in the transmitting trough is less than 1.0 mm thick.

8. The internal optical spectroscope of claim 1, wherein the distance from rim to rim between the next-to-last thread and the last thread is less than 3.08 mm.

9. A method of performing an optical biopsy in situ on targeted living tissue comprising the steps of:
    a) inserting a needle sleeve of an internal optical spectroscope into targeted living tissue, the needle sleeve holding a shaft, the shaft including a pointed insertion end and at least one v-shaped trough including an aft side and a next-to-aft side;
    b) pushing the shaft out of the needle sleeve and into the targeted living tissue without substantially damaging the targeted living tissue, the shaft being pushed out of the needle sleeve and into the targeted living tissue so that the at least one v-shaped trough of a screw shaft holds at least one fold of the targeted living tissue but does not remove or substantially damage any of the targeted living tissue while the shaft is being pushed out of the needle sleeve into the targeted living tissue or while the shaft is in the targeted living tissue; wherein the shaft comprises screw threads extending spirally along the outside surface of the shaft, with the v-shaped trough formed between aft and next-to-aft threads, a screw shaft is capable of being at least partially pushed out of the needle sleeve and screwed into the targeted living tissue when the needle sleeve is in the targeted living tissue, and the screw shaft also is capable of being unscrewed out of the targeted living tissue and back into the needle sleeve when the needle sleeve is in the targeted living tissue
    c) sending light from a light source comprising variable light wavelengths of both visible and near infrared light, the light being sent through at least one light transmission fiber stretching along a length of the shaft, the at least one transmission fiber comprising a transmitting end attached to either the next-to-aft side or the aft side of the at least one v-shaped trough, the at least one fold of the targeted living tissue being held in the v-shaped trough, so that the light from the light transmitting end penetrates through the at least one tissue fold, causing the at least one tissue fold to fluoresce light when the at least one tissue fold is held in the v-shaped trough;
    d) detecting fluoresced light from the at least one tissue fold, the fluoresced light being detected by a receptive end of at least one light detector fiber attached to an opposite side of the v-shaped trough from the transmitting end, the at least one light detector fiber stretching along a length of the screw shaft to a data processor;
    e) removing the shaft out of the targeted living tissue and back into the needle sleeve without removing or substantially damaging the targeted living tissue; and
    f) withdrawing the needle sleeve from the targeted living tissue.

10. The method of claim 9, wherein the transmitting end of the at least one light transmission fiber is attached at the next-to-aft side of the v-shaped trough, so that the light escapes directly out of the transmitting end on the next-to-aft side into the v-shaped trough.

11. The method of claim 10, wherein after the light is fluoresced from the tissue, the method further comprises a step of reflecting the fluoresced light from the at least one fold of the targeted living tissue in the v-shaped trough using a mirror-like reflector surface on the aft side of the v-shaped trough, so that the fluoresced light from the at least one fold of the targeted living tissue shines onto and is reflected by the mirror-like reflector surface and is detected by the receptive end of the at least one light detector fiber which is near the mirror-like receptor surface on the aft side of the v-shaped trough.

12. The method of claim 11, wherein the distance between the mirror-like reflector surface and the receptive end is no more than 1.0 mm.

13. The method of claim 9 wherein the transmitting end of the at least one light transmission fiber is positioned near to the aft side so that the light escapes out of the transmitting end to a right angle mirror which directs the light to escape out of the aft side of the v-shaped trough toward the next-to-aft side.

14. The method of claim 13, wherein the receptive end is on the next-to-aft side of the v-shaped trough.

15. The method of claim 13, wherein the at least one fold of tissue in the v-shaped trough is less than 1.0 mm thick.

16. The method of claim 13, wherein the distance from rim to rim between the next-to-last thread and the last thread is less than 3.08 mm.

17. An internal optical spectroscope comprising:
    a) a needle sleeve comprising a screw shaft, the needle sleeve being insertable into and removable from targeted living tissue;
    b) the screw shaft housed by the needle sleeve, the screw shaft being is capable of being at least partially pushed out of the needle sleeve and screwed into the targeted living tissue when the needle sleeve is in the targeted living tissue, and the screw shaft also is capable of being unscrewed out of the targeted living tissue and back into the needle sleeve when the needle sleeve is in the targeted living tissue, the screw shaft comprising a pointed insertion end and screw threads bonded to the outside surface of the screw shaft, the screw threads extending spirally along the outside surface of the shaft, with troughs formed between adjacent threads, the troughs being capable of holding at least one fold of targeted living tissue but not removing or substantially damaging any of the targeted living tissue while the shaft is being pushed out of the needle sleeve into the targeted living tissue, while the screw shaft is in the targeted living tissue in between the adjacent threads, or while the shaft is being removed from the targeted living tissue; wherein the shaft comprises screw threads extending spirally along the outside surface of the shaft, with the v-shaped trough formed between aft and next-to-aft threads, a screw shaft is capable of being at least partially pushed out of the needle sleeve and screwed into the targeted living tissue when the needle sleeve is in the targeted living tissue, and the screw shaft also is capable of being unscrewed out of the targeted living tissue and back into the needle sleeve when the needle sleeve is in the targeted living tissue c) a light source comprising variable light wave lengths of both visible and near infrared light;

d) at least one light transmission fiber comprising a transmitting end, the at least one light transmission fiber being connected to the light source and stretching along a length of the screw shaft, the light source being capable of sending light through the at least one light transmission fiber to the transmitting end positioned at a next-to-aft thread across the trough from an aft thread, the aft thread being the last thread the light encounters on the shaft, so that the light escapes out of the transmitting end and into the light transmitting trough between the next-to-aft thread and the aft thread, the light being capable of penetrating through the at least one fold of tissue and causing the at least one fold of tissue to fluoresce light when the at least one fold of tissue is held in the light transmitting trough;

e) a mirror-like reflector surface on the aft thread in the transmitting trough, the mirror-like reflector surface facing the next-to-aft thread across the light transmitting trough, the mirror-like reflector surface being capable of reflecting the light from the at least one fold of fluoresced tissue in the light transmitting trough;

f) at least one light detector fiber comprising a receptive end, the receptive end being positioned on the aft thread near the mirror-like reflector surface, the at least one light detector fiber stretching from the receptive end along the screw shaft to a data processor, the receptive end being capable of receiving the reflected light from the mirror-like reflector surface and transmitting an optical signal to the data processor; and g) the data processor.

18. The internal optical spectroscope of claim 17, wherein the distance from rim to rim between the next-to-aft thread and the last thread is less than 3.08 mm.

* * * * *